United States Patent [19]

Garrity et al.

[11] Patent Number: 5,064,856
[45] Date of Patent: Nov. 12, 1991

[54] NOVEL HMG-COA SYNTHASE INHIBITORS

[75] Inventors: George M. Garrity, Westfield; Robert Giacobbe, Lavallette, both of N.J.; Michael D. Greenspan, New York, N.Y.; Otto D. Hensens, Red Bank, N.J.; Henry Joshua, Staten Island, N.Y.; Maria T. D. Matas; Isabel Martin, both of Madrid, Spain; James A. Milligan, Robbinsville, N.J.; Sagrario M. del Val, Madrid, Spain; Walter Rozdilsky, Cliffwood Beach; Janet C. Onishi, Mountainside, both of N.J.; Jerrold M. Liesch, Princeton Junction, N.J.

[73] Assignee: Merck & Co., Inc., Rahway, N.J.

[21] Appl. No.: 387,668

[22] Filed: Jul. 31, 1989

[51] Int. Cl.$^5$ ................ A61K 31/365; C07D 307/94
[52] U.S. Cl. .................... 514/462; 514/473; 549/265; 549/331; 549/343
[58] Field of Search .......... 549/265, 331, 343; 514/462, 473

[56] References Cited

U.S. PATENT DOCUMENTS

| | | | |
|---|---|---|---|
| 4,751,237 | 6/1988 | Chabala et al. | 514/449 |
| 4,806,564 | 2/1989 | Chabala et al. | 514/449 |
| 4,816,477 | 3/1989 | Girotra et al. | 514/449 |
| 4,847,271 | 7/1989 | Chabala et al. | 514/336 |

FOREIGN PATENT DOCUMENTS

201/BOM/87  6/1987  India .

OTHER PUBLICATIONS

H. W. Fehlaker et al., J. Am. Chem. Soc., 110, 8242-8244 (1988).
DT 2821-189, 11-23-78, Japan.

Primary Examiner—C. Warren Ivy
Assistant Examiner—Ba K. Trinh
Attorney, Agent, or Firm—Melvin Winokur; Joseph F. DiPrima

[57] ABSTRACT

Compound of formulae (I) and (II) are HMG-CoA synthase inhibitors and exhibit antifungal activity.

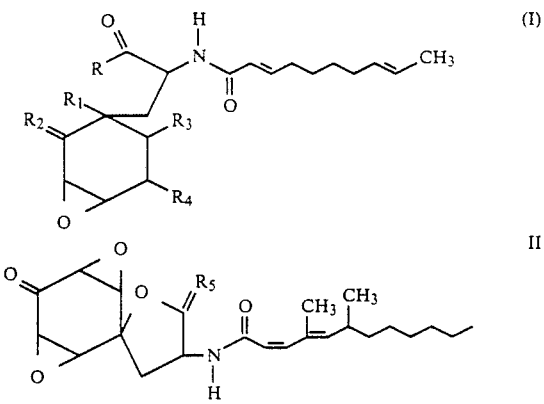

7 Claims, No Drawings

NOVEL HMG-COA SYNTHASE INHIBITORS

BACKGROUND OF THE INVENTION

A spirolactone compound (1) designated Aranorosin has been isolated from a fungal strain *Pseudoarachniotus roseus*.

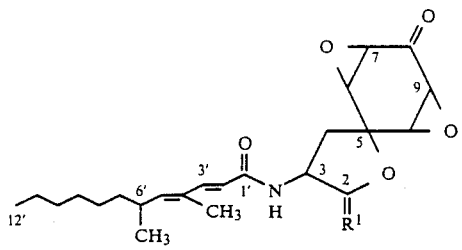

1: $R^1$ = H, OH
2: $R^1$ = H, OCOCH$_3$
3: $R^1$ = O

The compound (1) reported to be an antibiotic and its derivatives (2) and (3) were disclosed by H. W. Fehlaber and T. Mukhopadhyay et al J. Am. Chem. Soc., 110, 8242 (1988).

Certain 3,4 substituted β-lactones, exhibiting antihypercholesterolemic activity have been disclosed in U.S. Pat. No. 4,751,237 and copending application Ser. No. 021,848 filed Mar. 4, 1987 and Ser. Nos. 053,646, 053,774 filed May 26, 1987.

DETAILED DESCRIPTION OF THE INVENTION

The present invention is directed to novel compounds of structural formula (I) which are HMG—CoA synthase inhibitors:

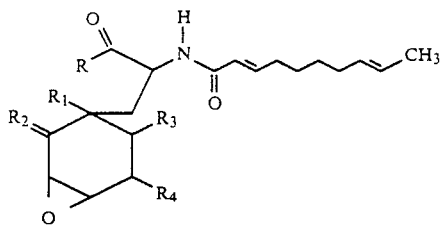

wherein:
R is OH, O—C$_{1-5}$alkyl;
R$_1$ is OH or R and R$_1$ together with the carbons to which they are attached form a γ-lactone;
R$_2$ is (H, OH) or O;
R$_3$ and R$_4$ are each OH, or R$_3$ and R$_4$ are joined to form an oxacyclopropane ring;
and to compounds of formula (II) as HMG—CoA synthase inhibitors:

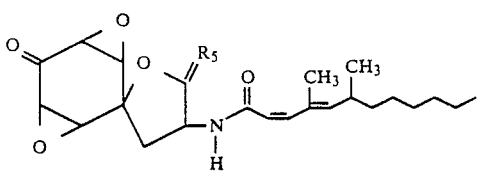

R$_5$ is
(a) (H, OH),
(b) (H, OCOCH$_3$), or
(c) O.

In one embodiment of this invention are the novel compounds of formula (I). Exemplifying this embodiment are the following compounds:

(A) 2,8-Decadienamide, N-(dihydro-6-hydroxy-5′-oxospiro(3,8-dioxatricyclo(5.1.0.0$^{2,4}$)octane-5,2′(3′H)-furan-4′-yl); and a stereoisomer identified by its nmr spectrum and labelled below as A-1;

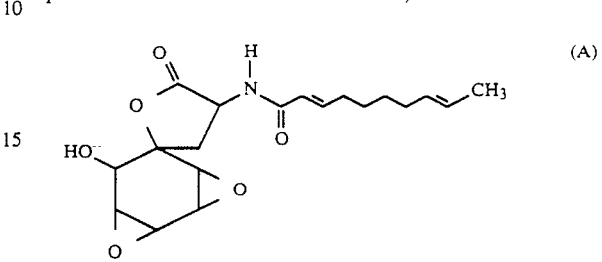

(B) 3,8-Dioxatricyclo(5.1.0.0$^{2,4}$)octane-5-propanoic acid, 5-hydroxy-6-oxo-.alpha.-((1-oxo-2,8-decadienyl)amino)-, methyl ester;

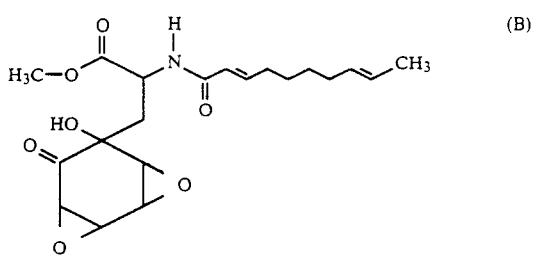

(C) 2,8-Decadienamide, N-(dihydro-5′,6-dioxospiro (3,8-dioxatricyclo(5.1.0.0$^{2,4}$)octane-5,2′-(3′H)-furan-4′-yl)-

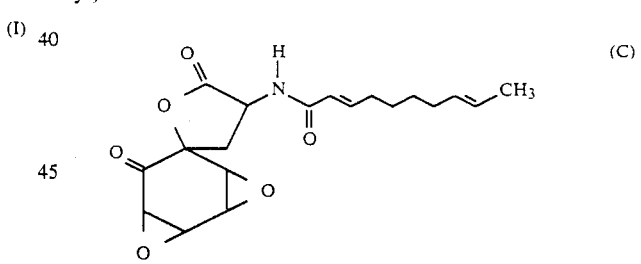

(A-2) N-(4,5-dihydro-4′,5′-dihydroxy-2′,5-dioxospiro[furan-2(3H),3′-[7]oxabicyclo[4.1.0]-hept]-4-yl)-2,8-decadienamide

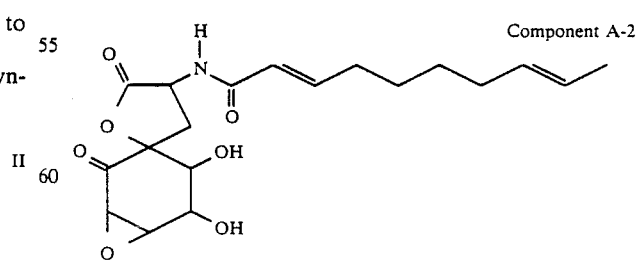

Component A-2

A second embodiment of this invention relates to a method of treating hypercholesterolemia employing a therapeutically effective amount of a compound of formula (I) or formula (II).

Compounds of formula (I) are prepared in a fermentation procedure employing a novel microorganism MF5253.

The fungus MF5253, recovered from an old pine litter, Salt Point, Sonoma County, Calif. has not formed any reproductive structures or characteristic features in the vegetative stage and is thus tentatively identified as a sterile mycelium.

The compounds of formula (II) were prepared as described in J. Am. Chem. Soc., 110, 8242 (1988).

Microscopic Observations

Colonies formed on malt-extract agar 40–50 mm in 4 days, which are hyaline to pale gray at the margins, becoming olive brown to olive black towards the center, Olive Brown, Dark Olive, Dark Grayish Olive, Fuscous-Black, Chaetura Black, Olivaceous Black (Capitalized color names from Ridgway, R. 1912. Color standards and nomenclature. Washington, D.C.).

Mycelium (in KOH) are hyaline to olivaceous brown, usually filamentous, moderately to densely branched, up to 12 um in diameter. Sometimes mycelium form multicellular, compact masses composed of intercalary chains or irregular aggregations of cells. The cells are thin- to thick-walled, up to 25 um in diameter, cylindrical, pyriform, to globose, olive gray, olive brown, to reddish brown, sometimes with tapered to filiform hyphal outgrowths. These cellular masses possibly function as hyphopodia or perithecial initials.

Microorganism MF5253 has been deposited with the American Type Culture Collection at 12301 Parklawn Drive, Rockville, Md. 20852 as ATCC 20953.

The present invention is also directed to a method of inhibiting cholesterol biosynthesis which comprises the administration to a subject in need of such treatment a nontoxic therapeutically effective amount of a compound represented by structural formula (I) or structural formula (II) and pharmaceutically acceptable salts thereof. Specifically the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethyl-ammonium hydroxide.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-tri-methylaminopropyl)iminotrimethylene dihalide]. The relative amounts of the compounds of this invention and these polymers is between 1:100 and 1:15,000.

The intrinsic HMG—CoA synthase inhibition activity of the compounds of this invention is measured by the standard in vitro protocol described below:

The livers from male Charles River CD rats (225–350 g) were homogenized in 0.25M sucrose which was adjusted with phenylmethylsulfonylfluoride (PMSF) and N-p-tosyl-l-lysine chloromethyl ketone (TLCK) so that the final concentration of each was 50 and 25 $\mu$g/ml, respectively. The homogenate was first centrifuged at 700$\times$g for 10 minutes, the supernatant decanted and recentrifuged at 7,700$\times$g for 20 minutes. This supernatant was filtered through a fine nylon screen to remove most of the fat layer and recentrifuged at 100,000$\times$g for 1 hour. This supernatant was removed and 1M potassium phosphate, dithiothreitol (DTT) and ethylene glycolbis($\beta$-aminoethyl ether)-N,N,N',N'-tetraacetic acid (EGTA) added to give a final concentration of 0.1M (pH 7.2), 0.5 mM and 0.1 mM, respectively. Solid ammonium sulfate was added to 50% saturation to the protein solution, it was centrifuged at 15,000$\times$g and the supernatant discarded. This precipitated protein could be stored at $-70°$ C. for at least one month with very little loss of activity. The ammonium sulfate precipitate was dissolved in an minimal amount of 0.06M potassium phosphate buffer (pH 7.2) containing 0.5 mM dithiothreitol and 0.1 mM EGTA (referred to as 0.06M phosphate buffer) and dialyzed overnight against 2 liters of the same buffer to remove the ammonium sulfate and to inactivate HMG—CoA lyase [Clinkenbeard, et al., J. Biol. Chem. 250, 3108–3116 (1975)].

The dialyzed extract was added to a column of DEAE-52 (Whatman) which had been equilibrated with 0.06M phosphate buffer (10 mg of protein to 1 ml bed volume of the resin). The DEAE-cellulose was eluted with 0.06M phosphate buffer until the optical density at 280 nm was essentially zero. This fraction contained the $\beta$-ketoacetyl-CoA thiolase activity. The HMG—CoA synthase was eluted from the column with 0.1M KCl in 0.06M phosphate buffer (pH 7.2) containing 0.5 mM DTT and 0.1 mM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded and the precipitate dissolved in a minimum of 0.06M phosphate buffer, pH 7.2 (about 10 ml) and the enzyme stored at $-80°$ C.

HMG—CoA Synthase Inhibition Assay

Enzyme protein (ca. 12.2 $\mu$g) was added to a solution containing 117 mM Tris-HCl (pH 8.0), 11.7 mM MgCl$_2$, 1.17 mM Ethylenediaminetetraacetic acid (EDTA), 0.58 mM dithiothreitol, and the indicated concentrations of the test compound (added as a 2 $\mu$g/ml solution in dimethylsulfoxide). The incubation took place in a volume of 0.085 ml at 30° in a shaking water bath. After 5 minutes, 15 $\mu$l of a solution containing acetoacetyl-CoA and 0.1 $\mu$Ci of 1-[$^{14}$C]-acetyl-CoA was added to give a final concentrations of 0.1 and 0.4 mM, respectively. The incubation was continued for 2 more minutes and the reaction stopped by the addition of 50 $\mu$l of the assay mixture to 0.2 ml of 6N HCl in a glass scintillation vial. The vial was heated for 1 hour at 110° after which time 0.2 ml more of 6N HCl was again added to each vial and the heating continued for another hour.

Following this, 1.0 ml of 0.9% saline was added to each vial and finally 10 ml of scintillation liquid. Radioactivity was determined in a Packard Tri-Carb liquid scintillation counter. Percent inhibition is calculated by the formula:

$$1 - \frac{\text{Sample} - \text{Blank}}{\text{Control} - \text{Blank}}$$

$IC_{50}$ values were determined by plotting the log of the concentration of the test compound verses the percentage inhibition and fitting a straight line to the resulting data by using the least squares method.

Representative of the intrinsic HMG—CoA synthase inhibitory activities of the compounds of this invention are the $IC_{50}$ data tabulated below:

| Compound | HMG-CoA Synthase $IC_{50}$ |
|---|---|
| A | $6.9 \times 10^{-6}$ M |
| B | $1.8 \times 10^{-7}$ M |
| C | $3.6 \times 10^{-7}$ M |
| A-1 | $> 10^{-5}$ M |
| A-2 | $2.5 \times 10^{-6}$ M |

The present compounds also demonstrate broad spectrum antifungal activity as measured in a Fungal Inhibitory Spectrum Profile (FISP). The compounds are particulary active towards filamentous fungus and yeasts including *Candida albicans*. Thus the present invention is also directed to a method of treating fungus infections which comprises the administration to a subject in need of such treatment of nontoxic therapeutically effective amount of a compound represented by the structural formula (I) and pharmaceutically acceptable salts thereof.

The compounds of this invention are adaptable to being utilized in various applications of antifungal compositions. In such use, compounds may be admixed with a biologically inert carrier, generally with aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected are antifungally effective amount of the compound of Formula I.

The following examples illustrate the preparation of the compounds of formula (I) and their incorporation into pharmaceutical compositions and as such are not to be considered as limiting the invention set forth in the claims appended hereto.

The composition of media employed in the following examples are listed below.

| KF SEED MEDIUM | per liter | Trace Element Mix | per liter |
|---|---|---|---|
| Corn Steep Liquor | 5 g | $FeSO_4 \cdot 7H_2O$ | 1 g |
| Tomato Paste | 40 g | $MnSO_4 \cdot 4H_2O$ | 1 g |
| Oat flour | 10 g | $CuCl_2 \cdot 2H_2O$ | 25 mg |
| Glucose | 10 g | $CaCl_2$ | 100 mg |
| Trace Element Mix | 10 ml | $H_3BO_3$ | 56 mg |
| | | $(NH_4)_6MoO_2 \cdot 4H_2O$ | 19 mg |
| pH = 6.8 | | $ZnSO_4 \cdot 7H_2O$ | 200 mg |
| F1 SOLID PRODUCTION MEDIUM | per 250 ml flask | *Base liquid | per liter |
| Cracked corn | 10 g | Ardamine pH | 0.2 g |
| Base liquid* | 10 ml | $KH_2PO_4$ | 0.1 g |
| | | $MgSO_4 \cdot 7H_2O$ | 0.1 g |
| | | Na Tartrate | 0.1 g |
| | | $FeSO_4 \cdot 7H_2O$ | 0.01 g |
| | | $ZnSO_4 \cdot 7H_2O$ | 0.01 g |
| | | no pH adjustment | |

Treatment of F1 media before inoculation:
1. Sterilize F1 for 20 minutes at 121° C.
2. Add 15 ml distilled $H_2O$ and reautoclave for 20 minutes at 121° C.

| PBE-2 LIQUID PRODUCTION MEDIUM | per liter | PBA-2 LIQUID PRODUCTION MEDIUM | per liter |
| --- | --- | --- | --- |
| Glycerol | 85 g | Glycerol | 85 g |
| Dextrose | 10 g | Dextrose | 10 g |
| Lard Water | 5 g | Lard Water | 5 g |
| Ardamine pH | 5 g | Ardamine pH | 5 g |
| $KH_2PO_4$ | 2 g | Corn Steep Liquor | 5 ml |
| Tomato Paste | 5 g | $(NH_4)_2SO_4$ | 2 g |
| $(NH_4)_2SO_4$ | 2 g | Corn Meal | 10 g |
| Glycine | 2 g | Pectin | 10 m |
| Cod Liver Oil | 2 ml | P-2000 | 2 ml |
| pH adjusted to | 7.0 | pH adjusted to | 7.0 |

EXAMPLE 1

Preparation of Compounds A, B, C, A-1 and A-2

A. Culture

Vegetative mycelia were prepared by inoculating a 250 ml unbaffled Erlenmeyer flask containing 54 ml of KF seed medium with the contents of a frozen vial of MF5253. Seed flasks were incubated for 3 days at 28° C. with agitation at 220 rpm and a 5-cm throw on a rotary shaker. Two ml of the resulting culture growth were used to inoculate either a solid or liquid production medium.

Solid Production Medium

The solid production medium F1 was incubated in 250 ml unbaffled Erlenmeyer flasks under static condition at 25° C. and 50% relative humidity for 14 days.

Liquid Production Medium

Forty-five ml of liquid production media, PBA-2 or PBE-2 were distributed into 250 ml unbaffled Erlenmeyer flasks. Flasks containing PBA-2 or PBE-2 were incubated at 25° C. and 50% relative humidity with agitation at 220 rpm on a rotary shaker with a 5-cm throw for 14 days. At harvest, cultures growing in the solid fermentation medium (F1) were extracted with 40 ml of 75% methanol; cultures growing in liquid fermentation media (PBA-2 to PBT-2) were extracted with 40 ml of 100% methanol.

B. Isolation

Step 1. A 14 liter fermentation from a stirred reactor was extracted by addition of an equal volume of methanol, filtered and concentrated to 2.4 liter.

Step 2. The concentrate from Step 1 was extracted with chloroform. Solvent was removed from the extract yielding 33 grams of non-volatile residue of which approximately 4 grams were due to the A-2, A-1, A, B and C components.

Step 3. The residue from Step 2 was chromatographed on a 4 liter LH-20 (Pharmacia, Piscataway, N.J.) column in methanol. The middle cut containing the A-2, A-1, A, B and C components was concentrated and rechromatographed on the same 4 liter, LH-20 column in methanol taking 15 ml fractions. Fractions 170-205 contained mainly components A-2, A-1 and B with a combined weight of 3.3 gm. Fractions 206-250 contained components A and C with a combined weight of 1.3 gm.

Step 4. The residue of fractions 170-205 from Step 3 after removal of solvent was chromatographed on a column of 70 gram slurry-packed silica gel 60, 70-230 mesh (EM Science, Cherry Hill N.J.) using a step gradient and taking 15 ml fractions.

| Fraction # | Eluent Composition | |
| --- | --- | --- |
| | % Hexane | % Ethylacetate |
| 1-20 | 65 | 35 |
| 21-100 | 55 | 45 |
| 101-180 | 45 | 55 |
| 181-220 | | 100 |

Fractions 46-79 contained components B and C with a total weight of 535 mg. Fractions 125-185 contained components A-2 and A-1 with a total weight of 449 mg.

Step 5. The residue from fractions 206-250 from Step 3 were charged to a silica gel column prepared as in Step 4 and eluted with a step gradient.

| Fraction # | Eluent Composition | |
| --- | --- | --- |
| | % Hexane | % Ethylacetate |
| 1-40 | 65 | 35 |
| 41-120 | 50 | 50 |
| 121-200 | 40 | 60 |

Fractions 58-80 contained mainly component C with some component A for a total weight of 650 mg. Fractions 81-120 contained pure component A for a total weight of 400 mg.

Step 6. The residue from fractions 58-80 from Step 5 was chromatographed on silica gel as in Step 4 except that the step gradient was as follows:

| Fraction # | Eluent Composition | |
| --- | --- | --- |
| | % Hexane | % Ethylacetate |
| 1-20 | 65 | 35 |
| 21-100 | 55 | 45 |

Fractions 46-65 contained component C, however, fractions 51-65 were concentrated to yield 445 mg of C which crystallized.

Step 7. The residue from fractions 46-79 from Step 4 was chromatographed on a 21.4 mm ID×25 cm $C_{18}$ preparative column with an 21.4 cm ID×5 cm guard column (Rainin Instrument Co) at 60° C. using an eluent composition of 40:60 v/v acetonitrile-water at 10 ml/min. collecting 1 fraction/minute. Fractions 23-32 were combined and extracted with ethyl acetate. The ethyl acetate layer yielded 235 mg of component B.

Fractions 37-49 were combined and extracted with ethyl acetate. Concentration of the ethyl acetate layer yielded 189 mg of component C which crystallized on standing.

Step 8. The residue from fractions 125-185 from Step 4 was chromatographed in the same $C_{18}$ column described in Step 7 run at 60° C. except that the eluent composition was 35:65 v/v acetonitrile-water.

Fractions 19-25 were combined and extracted with ethyl acetate. Concentration of the ethyl acetate extract yielded 105 mg of component A-2.

Fractions 33-41 were combined and extracted with ethyl acetate. Concentration of the ethyl acetate extract yielded 174 mg of component A-1.

Compounds A, B, C, A-1 and A-2 were identified by their $^{13}$C NMR spectrum given below:

Chemical shifts are given in ppm relative to tetramethylsilane at zero ppm using the solvent peak of the methyl group at 1.3 ppm as internal standard.

Compound A 2,8-Decadienamide, N-(dihydro-6-hydroxy-5'-oxospiro(3,8-dioxatricyclo(4.1.0.0$^{2,4}$)octane-5,2'-(3'H)-furan-4'-yl)-.

$^{13}$C NMR Chemical Shifts (CD$_3$CN, 75 MHz): 18.1 28.4, 29.8, 32.4, 32.95, 33.06, 50.9, 52.6, 54.0, 56.3, 57.5, 69.8, 85.4, 123.8, 125.8, 132.2, 146.4, 166.7, 175.4 ppm. Mass spec. M$^+$ = 363.1689.

Compound B 3,8-Dioxatricyclo(5.1.0.0$^{2,4}$)octane-5-propanoic acid, 5-hydroxy-6-oxo-.alpha.-((1-oxo-2,8-decadienyl-)amino), methyl ester.

$^{13}$C NMR Chemical Shifts (CD$_3$CN, 75 MHz): 18.1 28.4, 29.8, 32.4, 32.9, 38.3, 48.2, 53.0, 53.4, 57.2, 60.04, 60.13 77.1, 124.1, 125.8, 132.2, 146.2, 166.6, 172.9, 203.7 ppm. Mass spec. M$^+$ = 393.1769.

Compound C 2,8-decadienamide, N-(dihydro-5',6-dioxospiro-(3,8-dioxatricyclo(5.1.0.0$^{2,4}$)octane-5,2'-(3'H)-furan-4'-yl)-.

$^{13}$C NMR Chemical Shifts (CD$_3$CN, 75 MHz): 18.1 28.4, 29.8, 32.4, 32.9, 38.5, 48.8, 53.7, 56.4, 57.1, 58.8, 84.1, 123.6, 125.8, 132.2, 146.8, 166.6, 174.2, 199.0 ppm. Mass spec. M$^+$ = 361.1538.

Compound A-1

Stereoisomer of A.

$^{13}$C NMR Chemical Shifts (CD$_3$CN, 75 MHz): 18.1 28.4, 29.8, 32.4, 32.9, 35.1, 49.1, 50.3, 53.9, 54.1, 58.5, 69.9, 81.5, 123.7, 125.8, 132.2, 146.5, 166.6, 174.7 ppm. Mass spec. M$^+$ = 363.1687.

Compound A-2

N-(4,5-dihydro-4',5'-dihydroxy-2',5-dioxospiro[furan-2'(3'H),3'-[7]oxabicyclo[4.1.0]hept]-4-yl)-2,8-decadienamide.

$^{13}$C NMR Chemical Shifts (CD$_3$CN, 75 MHz): 18.1 28.4, 29.8, 31.1, 32.4, 32.9, 48.9, 56.1, 59.7, 69.9, 76.6, 87.1, 123.7, 125.7, 132.2, 146.7, 166.7, 174.7 201.2 ppm. Mass spec. M$^+$ = 379.1631.

EXAMPLE 2

As a specific embodiment of an oral composition of a compound of this invention, 20 mg of the lactone from Example 1 is formulated with sufficient finely divided lactose to provide a total amount of 580 to 590 mg to fill a size 0 hard gelatin capsule.

EXAMPLE 3

As a specific embodiment of a parenteral composition of a compound of this invention, 20 mg of the lactone from Example 1, as the sodium salt, is dissolved in sterile water, buffered to a pH of 7 with 1.0 mM potassium phosphate buffer solution to a concentration of 2.0 percent and is placed in a sterile ampoule for parenteral administration.

What is claimed is:

1. A compound of structural formula (I):

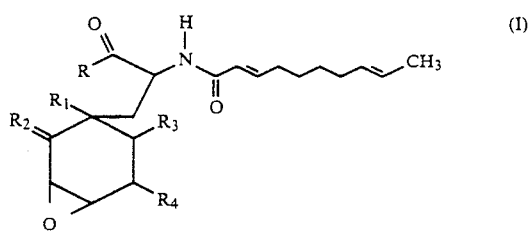

wherein:

R and R$_1$ together with the carbons to which they are attached form a γ-lactone;
R$_2$ is geminal H and OH or O;
R$_3$ and R$_4$ are each OH or R$_3$ and R$_4$ are joined to form an oxacyclopropane ring.

2. A compound (C) of claim 1 wherein: R$_3$ and R$_4$ form an oxacyclopropane ring; which is 2,8-Decadienamide-N-(dihydro-5',6-dioxospiro-3,8-dioxatricyclo(5.1.0.0$^{2,4}$)octane-5,2'(3H)-furan-4'-yl).

3. A compound (A) of claim 1 wherein: R$_2$ is H, OH, and R$_3$ and R$_4$ form an oxacyclopropane ring; which is 2,8-decadienamide, N-(dihydro-6-hydroxy-5'-oxospiro-(3,8-dioxatricyclo(4.1.0.0$^{2,4}$)octane-5,2'(3'H)-furan-4'-yl)-, and in which the $^{13}$C NMR shifts are 18.1 28.4, 29.8, 32.4, 32.95, 33.06, 50.9, 52.6, 54.0, 56.3, 57.5, 69.8, 85.4, 123.8, 125.8, 132.2, 146.4, 166.7, 175.4 ppm.

4. A compound (A-1) of claim 1 wherein: R$_2$ is H, OH, and R$_3$ and R$_4$ form an oxacyclopropane ring; which is 2,8-decadienamide, N-(dihydro-6-hydroxy-5'-oxospiro-(3,8-dioxatricyclo(4.1.0.0$^{2,4}$)octane-5,2'(3'H)-furan-4'-yl)-, and in which the $^{13}$C NMR shifts are 18.1 28.4, 29.8, 32.4, 32.9, 35.1, 49.1, 50.3, 53.9, 54.1, 58.5, 69.9, 81.5, 123.7, 125.8, 132.2, 146.5, 166.6, 174.7 ppm.

5. A compound (A-2) of claim 1 wherein: R$_2$ is O and R$_3$ and R$_4$ are each OH which is N-(4,5-dihydro-4',5'-dihydroxy-2',5-dioxospiro[furan-2'(3'H),3'-[7]oxabicyclo[4.1.0]-hept]-4-yl)-2,8-decadienamide.

6. A pharmaceutical composition for the treatment of hypercholesterolemia which comprises a non-toxic effective amount of a compound of claim 1 and a pharmaceutically acceptable carrier.

7. A method of inhibiting cholesterol biosynthesis in a subject which comprises the administration to the subject in need of such treatment a non-toxic therapeutically effective amount of a compound of claim 1 to inhibit cholesterol biosynthesis.

* * * * *

UNITED STATES PATENT AND TRADEMARK OFFICE
CERTIFICATE OF CORRECTION

PATENT NO. : 5,064,856
DATED : November 12, 1991
INVENTOR(S) : G. M. Garrity et al It is certified that error appears in the above-identified patent and that said Letters Patent is hereby corrected as shown below:

Title page, item [75], "Robert Giacobbe" should be --Robert A. Giacobbe--.

Signed and Sealed this

Twenty-second Day of June, 1993

Attest:

MICHAEL K. KIRK

*Attesting Officer*     *Acting Commissioner of Patents and Trademarks*